United States Patent [19]
Bennett et al.

[11] Patent Number: 5,389,097
[45] Date of Patent: Feb. 14, 1995

[54] ENHANCED MONITORING DEVICE FOR SURGICAL GLOVES AND OTHER BARRIERS

[75] Inventors: John K. Bennett, Houston; Mark Maxham, Richardson; William H. Marshall; Robert E. Williams, both of Houston, all of Tex.

[73] Assignee: Novatec Medical Products, Inc., Houston, Tex.

[21] Appl. No.: 277,984

[22] Filed: Jun. 22, 1994

Related U.S. Application Data

[63] Continuation of Ser. No. 846,539, Mar. 4, 1992, abandoned, which is a continuation-in-part of Ser. No. 528,926, May 25, 1990, Pat. No. 5,114,425.

[51] Int. Cl.⁶ .................................. A61B 17/36
[52] U.S. Cl. .............................. 606/34; 340/540
[58] Field of Search ............. 606/32, 34; 340/540

[56] References Cited

U.S. PATENT DOCUMENTS

| | | | |
|---|---|---|---|
| 4,956,635 | 9/1990 | Langdon | 606/34 X |
| 5,036,309 | 7/1991 | Dennison, Jr. | 606/34 X |
| 5,109,215 | 4/1992 | Dennison . | |
| 5,114,425 | 5/1992 | Williams et al. | 606/34 |
| 5,157,379 | 10/1992 | Dennison | 606/34 X |
| 5,204,632 | 4/1993 | Leach | 324/557 |

FOREIGN PATENT DOCUMENTS 712082  1/1980  U.S.S.R. .................... 606/34

Primary Examiner—Lee S. Cohen
Attorney, Agent, or Firm—Pravel, Hewitt, Kimball & Krieger

[57] ABSTRACT

A monitoring device for detecting adulteration of an article used in critical use applications such as a surgical glove where the gloves are worn by the surgeon and are exposed to the body fluids of a patient. The device includes the detection of a particular value of electrical condition, preferably resistance or impedance, as well as the first and second derivatives of electrical condition. These values are monitored in a substantially continuous manner and are smoothed and filtered to determine when a hole or thin spot in the glove occurs. In addition, the device includes an autoranging function which maintains the measured voltage in a prescribed range, thus allowing the device to operate at a higher level of accuracy for a greater period of time than a device without the feature. Also, the device warns the health care professional when the electrical properties of the gloves have degraded to a point where the device may no longer reliably detect holes in the gloves.

32 Claims, 10 Drawing Sheets

HYDRATION | HOLE

ENHANCED MONTORING DEVICE FOR SURGICAL GLOVES AND OTHER BARRIERS

This is a continuation of application Ser. No. 07/846,539, filed on Mar. 4, 1992, now abandoned which application is a continuation-in-part of application Ser. No. 07/528,926, filed May 25, 1990, now U.S. Pat. No. 5,114,425, for "Method and Apparatus For Detecting Actual or Likely Adulteration of Critical Use Gloves."

FIELD OF THE INVENTION

This invention relates to the detection of adulteration of critical use articles, such as gloves used during surgery or other medical procedures, condoms, surgical gowns, or other barriers, in order to detect this adulteration as soon as technically possible. This early detection reduces the risk of exposure of the wearer of the invention to the body fluids of patients. Early detection further protects patients from the body fluids of the person wearing the gloves.

BACKGROUND OF THE INVENTION

The adulteration of critical use articles such as surgical gloves and condoms poses considerable health risks. Adulteration as used herein is intended to encompass conditions such as holes formed during manufacture of the article as well as holes formed thereafter for any reason, which holes provide a path for adulteration of the article by potentially dangerous fluids such as body fluids. The term "holes" or "perforations" includes not only holes capable of initially passing fluid but also incipient holes, which may, initially, be too small to pass amounts of fluid but may enlarge over time, or otherwise breach or deteriorate the integrity of the barrier posed by the article. Such holes may even form a danger before reaching a size large enough to pass actual fluid since bacteria may theoretically pass through even smaller openings; but, it is more likely that a fluid carrier is needed to carry the bacteria through the membrane.

One example of a critical use article is the surgical glove. Although problems associated with surgical gloves are discussed below, it is understood that similar problems are presented by other articles such as condoms, surgical gowns, surgical drapes, etc. The adulteration of gloves used in surgery has long been a problem to the medical doctor or other health care worker. There are two common sources for the creation of holes or perforations in surgical gloves prior to and during use. One source is the manufacturer who, due to lack of quality control or inherent manufacturing problems, may manufacture and sell gloves which already have perforations. In about 1990, the Federal Food and Drug Administration has determined, by field inspection, failure rates of three to sixteen percent in surgical gloves prior to use. The FDA further found that, for patient-examination gloves, average defect rates range from fourteen to eighteen percent. In a recent attempt to tighten the quality control in surgical gloves, the FDA has resorted to its own modification of the well-known and fundamental A.S.T.M. technique for determining defects in gloves—a water fill test. The water fill test is only capable of detecting holes large enough to pass visually detectable amounts of water. Danger exists when a hole is large enough to expose skin on the other side of the glove to harmful bacteria or virus even though the hole may not be large enough to actually allow visible amounts of water to pass through the hole during the water fill test.

The second source of holes or perforations in gloves occurs during use. For example, holes or dangerously thin spots may develop in gloves at the time that the surgeon first fits the gloves over his or her hands, or, a glove may be perforated during surgery. Perforations during surgery can occur because of penetration by sharp objects or because of the breaking down of inherently thin spots in the gloves or areas made thin as a result of putting the glove on the hand or manipulating instruments. Perforations expose the surgeon to actual or possible contact with patient body fluids because of the resulting adulteration of the surgical gloves. While such adulteration has always been a possible source of infection or the spreading of bacteria to the surgeon or from the surgeon to the patient, the alarming spread of the hepatitis and AIDS viruses has created an even more serious problem—the possible spread of an incurable disease from the patient to the surgeon or from the surgeon to the patient. Therefore, the need for accurate and immediate detection of actual or near-adulteration in surgical gloves is now at a heightened level because of the potential for the spread of incurable diseases from patient to surgeon or vice-versa.

The problem with the AIDS virus is not limited, however, to surgeons or other persons in the operating room such as nurses and anesthesiologists. For example, it is possible that other users of critical use gloves such as dentists or paramedics may be subject to many of the same serious concerns because the dentist or paramedic is also exposed to body fluids during his or her work on a patient. While perhaps less likely, there is also some possibility for the spread of serious diseases from patients to doctors during physical examinations. For purposes of definition, doctors, dentists, nurses and others who may be exposed to disease through gloves or other barriers are defined herein as "health care workers." It is also noted that the problem of communication of a disease between persons due to adulteration of a material acting as a barrier between the persons is not limited to surgical gloves, but other articles such as surgical gowns, masks and condoms present similar problems.

While the FDA has taken the approach of using the rudimentary method of simple water fill to determine leaks in gloves as manufactured, such simple techniques cannot be used to detect adulteration in gloves during use. There have been some attempts in the prior art to detect the occurrence of perforations in surgical gloves after the gloves are on the doctor's hands, all of which use resistance level detection as the parameter to detect holes. Such level detection concepts have been known for several decades and recently there have been further efforts at modest improvement on such detection mechanisms, all continuing to rely on resistance level detection as the principal parameters to be measured.

U.S. Pat. No. 4,321,925 of John Hoborn and Ulrich Krebs discloses an electronic detector arranged so that the level of electronic conductivity through the gloves and between the patient and the surgeon may be sensed at regularly recurring discrete time intervals in order to measure a predetermined level of sensed conductivity and signal an alarm if such predetermined level is met. The detecting circuit of the '925 patent is actually located in one of the shoes of the surgeon and includes one contact located in the insole of the shoe in order to make electrical contact with the surgeon and a second contact exposed to an electrically conducting plate located on the floor of the operating room so that a closed circuit is formed between the operating table, the patient, the doctor, the electronic device located in the shoe and the round conducting element or plate located on the floor of the operating room. The '925 patent teaches that five times per second the disclosed circuit short-circuits the contacts in the insole and in the bottom of the sole of the shoe in order to discharge static electricity from the insole contact which may have accumulated from the doctor. After each short circuit, the circuit is opened between the two contacts and a voltage level sensor is used to detect the level of electrical conductivity which occurs externally between the contacts.

The impedance of the rubber or latex that comprises the surgical gloves is high. If there is a perforation in the operating gloves of the surgeon, the impedance is thereby reduced and a greater conductivity is provided through the gloves. The '925 patent teaches that the occurrence of a perforation in the operating gloves may result in a relatively high electric conductivity between the surgeon and patient, thus allowing the sensing device to sound an alarm upon the occurrence of a predetermined level of sensed conductivity.

Setting of the appropriate level of conductivity is strictly a matter of design and thus it is believed that one drawback to the device of the '925 patent is that the level of conductivity required to trigger the alarm may differ from glove to glove, depending upon the nature of the material, the thickness of the material and any other factors which may impact upon the general conductivity of the series circuit, which includes not only the doctor and patient, but also the doctor's shoes, a round plate located on the operating floor, and the operating table itself. Therefore, the '925 patent may work fairly well for certain types of gloves whose characteristics conform to the particular resistance level chosen for the resistance level sensor, but the '925 patent may not work well with many other types of gloves. In order to function properly, the resistance level sensor in the '925 patent would have to be adjusted to some pre-determined level depending on the type of gloves used.

Perhaps more importantly, the tendency of latex gloves to absorb fluid during use is a factor not solved by the '925 Hoborn patent and other similar resistance level detection devices. Most natural rubber latex gloves absorb considerable quantities of water with time, referred to as hydration. This hydration effect causes the conductivity of the glove to increase markedly, thus decreasing its resistance. Eventually, the electrical resistance of the gloves becomes as low as a glove with a hole in it. Thus for many types of surgeons' gloves, devices like that shown in the '925 patent will eventually give a hole alarm when there is no perforation. Therefore, the fact that the absolute conductivity of a glove varies with the hydration of the glove material detracts from the effectiveness of the sensor of the '925 device. There are other patents which disclose level detection type devices which are believed to have disadvantages similar to the '925 patent. See U.S. Pat. Nos. 4,956,635 of Langdon and 5,036,309 of Dennison.

Other prior art devices include several devices that utilize a basin of conductive fluid in which the surgeon places his or her gloved hands for the purposes of determining whether or not the gloves have become adulterated. See U.S. Pat. Nos. 2,981,886 of Beck; 4,810,971 of Marable; 4,909,069 of Albin; and 4,956,635 of Langdon. If the conductive fluid in the basin enters a gloved hand or comes in contact with body fluid already in the adulterated glove, increased conductivity is detected. Other devices and relevant prior art are discussed in an Information Disclosure Statement.

It is submitted that there is need for the development of further, more sophisticated detection methods and apparatus in order to detect adulteration of surgical or other critical use gloves. This detection method should also preferably not interfere with the normal activities of the user. In addition, there is a need for detection methods which do not necessarily depend on the absolute level of conductivity of particular gloves, but are capable of detecting rapid changes in glove condition. Also, it is desirable for the detection method to be able to reliably monitor the integrity of gloves for an extended period of time and to be adaptable to different glove types from different glove manufacturers.

One solution is found in the parent patent application Ser. No. 07/528,926, which teaches a technology of detection of the rate of change of electrical properties in barriers such as critical use surgical gloves.

SUMMARY OF THE INVENTION

The present invention comprises a new and improved monitoring device for detection of holes in gloves and other barriers. The monitoring device according to the present invention can reliably monitor the integrity of gloves for an extended period of time and is suitable for use with a number of different glove types from different glove manufacturers. The monitoring device is a programmable, configurable, and self-adapting device. The device continuously measures the resistance, the rate of change or first derivative of resistance, and the rate of change or second derivative of resistance across the gloves worn by the health care worker in a circuit comprised of the patient, the health care worker, and the gloves. The device distinguishes between changes in resistance caused by a hole or puncture in the glove and changes in resistance caused by normal glove hydration.

When the system is turned on, a number of variables are initialized and the device is configured to a certain risk level. On certain high risk operations, the configuration of certain variables can be adjusted so that the alarm is activated more easily and therefore detects an even smaller adulteration than does the standard configuration. The device continually monitors the voltage level applied across the gloves and performs an autorange function to maintain the voltage level in a desired range, where the devices measurement capability is most acute. The autorange function ensures that, as the gloves become hydrated due to use, the current supplied across the gloves is adjusted upward accordingly to maintain the voltage level in the prescribed range. This significantly increases the length of time that the gloves can be reliably monitored. In addition, the device continuously monitors the resistance across the gloves in the presence of substantial amounts of electrical noise and executes a smoothing function across the obtained resistance values using a combination of linear and non-linear filters. These software filters improve the reliability of the system by decreasing the possibility of erroneous resistance values causing false alarms. The linear filters employ averaging, and the non-linear filter employs a 5-point median filter.

The device computes the first and second derivatives of the resistance across the gloves and uses these values to aid in determining if a hole or puncture condition is likely to have occurred. The device preferably operates such that, if the resistance across the gloves drops below a certain threshold value, referred to as the ARMING POINT and either the first or second derivative values of the resistance across the gloves indicate that a puncture condition may have occurred, the device enters an ARMED condition, indicating that the first step has been taken toward sounding the hole alarm. If the device is armed, and if the resistance across the gloves then drops below a second critical threshold value referred to as the HOLE POINT, then the END-OF-USE ALARM is sounded. The END-OF-USE ALARM is primarily an indicator of a hole or puncture in the glove, but may also be signalled when the glove is unsafe to wear due to the risk of shock hazard to health care workers. If the device is ARMED for a period of time greater than a preset value, and the resistance does not drop below the HOLE POINT, then the device is disarmed, it being assumed that the armed condition did not represent a breach in the glove barrier, but rather a period of rapid hydration.

If the gloves reach a certain level of hydration wherein the resistance drops below a certain minimum value referred to as HYDRATION POINT, and the device is not ARMED, then a END-OF-USE WARNING is indicated. The END-OF-USE WARNING is an advisory signal that warns of a glove condition requiring regloving in the near future. This gives the health care worker time to plan to reglove when most convenient and when patient safety permits. This signal is generated when the resistance across the glove is approaching the point where the device may not be able to reliably determine if a hole or puncture occurs in the gloves. Therefore the END-OF-USE WARNING warns the health care worker to reglove at the earliest convenience.

Thus, this invention comprises a device that continually monitors the resistance across a pair of gloves, as well as the first and second derivatives of resistance, to detect punctures or holes in the gloves. The device continually monitors and adjusts the current generated through the gloves as the gloves become hydrated over time to increase the length of time that gloves can be reliably monitored. When the resistance across the gloves drops below a certain warning value, then the surgeon is advised that the gloves should be changed. It should be noted that one distinguishing feature of the present invention over all other prior art devices is that, even if a glove gradually hydrates below some predetermined resistance level that would at least theoretically alarm prior art devices, the device according to the present invention will not signal an END-OF-USE ALARM. The reason is that the device according to the present invention requires a rapid drop in resistance (large first or second derivative) immediately prior to reaching a predetermined low resistance level in order to activate the END-OF-USE ALARM.

In an alternate embodiment, the monitoring device generates pulses of time-varying current, either AC or pulsating DC, across the gloves or other barrier being tested. This allows the electrical characteristics, in particular the resistance and capacitive reactance components of the barrier impedance, of the gloves or barrier to be fully characterized, thus providing enhanced testing accuracy.

The descriptions in the "Summary of the Invention" are not intended to describe all embodiments or features which are more fully described in the "Description of the Preferred Embodiment" to follow. Further, it is intended that the patent protection sought and obtained be reflected in the claims and not this Summary.

BRIEF DESCRIPTION OF THE DRAWINGS

A better understanding of the present invention can be obtained when the following detailed description of the preferred embodiment is considered in conjunction with the following drawings, in which.

DETAILED DESCRIPTION OF THE PREFERRED EMBODIMENTS

Figure 1:
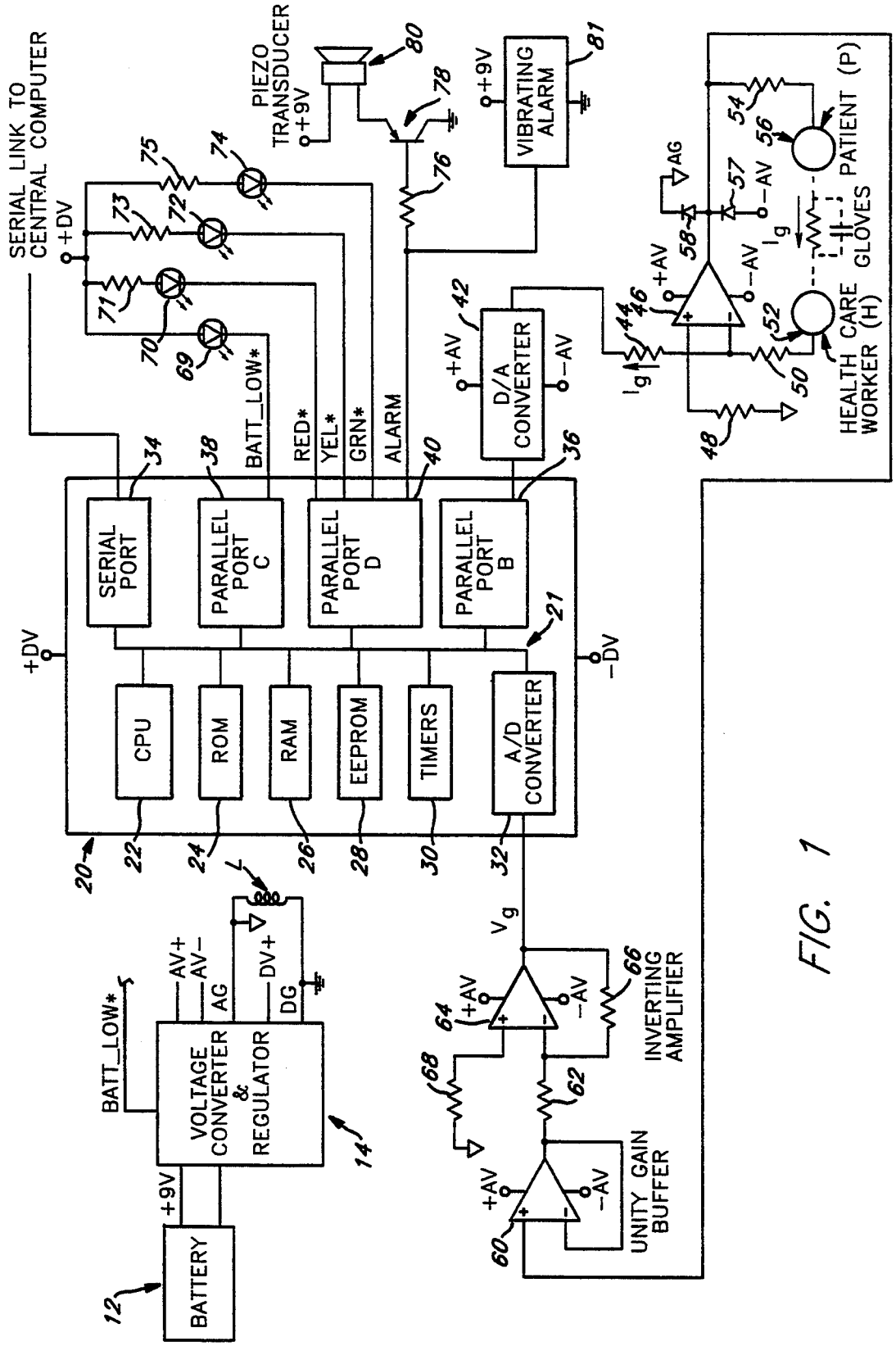
FIG. 1 is a block diagram of the glove monitoring device according to the preferred embodiment of the invention.

Referring now to FIG. 1, the monitoring device according to one preferred embodiment is shown. In the preferred embodiment, the monitoring device is used to monitor the condition of surgical gloves. However, it will be appreciated that the monitoring device can be used to monitor the condition of other articles that act as a barrier between persons to prevent the transmission of bodily fluids or other dangerous fluids. Thus, the monitoring device can be used to monitor other articles including, but not limited to, condoms, surgical gowns, surgical masks, and surgical drapes.

The monitoring device includes a battery 12 that generates 9 volts that is provided to a voltage converter and regulator 14. The battery 12 also preferably provides a logical ground to the voltage converter and regulator 14. The voltage converter and regulator 14 receives the nine volts and generates voltage outputs referred to as AV+, AV−, AG, DV+ and DG. In the preferred embodiment, AV+ is +6 Volts DC, AV− is −6 Volts DC and DV+ is +5 Volts DC. In addition, AG is an analog ground and DG is a digital ground. In the preferred embodiment, AG and DG are connected at a single point through a low impedance inductor L, so as to avoid ground loops. The voltage converter and regulator 14 also generates a battery low voltage alarm signal referred to as BATT_LOW*. As described below, the BATT_LOW* signal lights an LED when the voltage drops below a certain value. The BATT_LOW alarm is independant of the other device alarms, which are generated by the microprocessor. Thus, the battery low voltage alarm will function even if the battery voltage is too low to operate the other alarm circuitry.

The monitoring device includes a processing system or microcontroller 20. The microcontroller 20 is preferably the MC68HC11 microcontroller produced by Motorola Semiconductor, Inc. although other controllers can be used. For more information on the Motorola MC68HC11, the HCMOS MC68HC11 single chip microcontroller technical data book, published by Motorola, which is hereby incorporated by reference, should be consulted. The microcontroller 20 is powered by voltages DV+ and DV−, as shown. The microcontroller 20 includes a CPU 22, read only memory (ROM) 24, random access memory RAM 26, EEPROM (Electrically Erasable Programmable Read Only Memory) 28, various timers 30, and a block circuit 32 comprising four analog to digital (A/D) converters. The microcontroller 20 also includes a serial port 34 and parallel ports referred to as port B 36, port C 38 and port D 40. The serial port 34 is preferably used to provide information through a serial link to a central computer (not shown). Each of the various elements comprising the microcontroller 20 are interconnected through a shared bus 21, as shown.

Parallel port B 36 is an 8-bit port and outputs eight bits of data, referred to as PB<0:7>, to a digital to analog (D/A) converter 42. The D/A converter 42 is powered by voltages AV+ and AV−, as shown. The D/A converter 42 includes a current to voltage converter (not shown) and outputs a voltage proportional to the eight-bit value of data provided by the parallel port B 36. The voltage output from the D/A converter 42, referred to as Vout, can be computed as follows:

$$V_{out} = 4.6 \times \left( \frac{PB0}{2} + \frac{PB1}{4} + \frac{PB2}{8} + \frac{PB3}{16} + \frac{PB4}{32} + \frac{PB5}{64} + \frac{PB6}{128} + \frac{PB7}{256} \right) \text{Volts}$$

In this formula, 4.6 represents the supply voltage to the D/A converter (6 Volts DC) 42 less two diode drops (of 0.7 Volts DC each). Therefore, the D/A converter 42 outputs a voltage between zero and 4.6 volts.

The output of the D/A converter 42 is coupled through a resistor 44 to the inverting input of an operational amplifier (op amp) 46, thus creating a controlled current source that establishes the current applied to the doctor-patient interface (the glove). This current is proportional to D/A converter 42 output voltage Vout. Since the inverting input of op amp 46 is at virtual ground, the glove current Ig is determined by Ohm's law and is equal to Vout/$R_{44}$. The current that flows through the resistor 44 is designated as Ig. The current Ig is shown in the direction away from the inverting input of the op amp 46 to the D/A converter 42 as the chosen convention. The non-inverting input of the op amp 46 is connected through a resistor 48 to an AG and reduces the offset bias error of op amp 46. Op amp 46 is powered by AV+ and AV−. The inverting input of the op amp 46 is also connected through a resistor 50 to a jack 52, which is connected via a lead to the respective health care worker H using the gloves that are to be tested. As shown, the gloves can be modeled as a resistor in parallel with a capacitor. The resistance across the gloves is designated as Rn. The output of the op amp 46 is connected through a resistor 54 to a jack 56, which is connected via a lead to the patient P being examined. The op amp 46 acts as a current source, providing current through the resistor 54, the patient P via the lead connected to jack 56, through the gloves and to the health care worker H via the lead connected to jack 52 and back up through the resistors 50 and 44 (since no current flows into op amp 46). Thus, a circuit is formed between the health care worker H, the patient P, and the gloves being worn by the health care worker H. The resistors 50 and 54 limit the maximum current applied to the patient/health care worker interface to less than 10 milliamperes, even in the case of a catastrophic circuit failure. The current flowing through the gloves (Ig) is proportional to the voltage Vout output from the D/A converter 42. When Vout is its maximum value of approximately 4.6 volts, the current Ig flowing through the gloves is 9.7 microamperes. When Vout is at its minimum value of approximately 0.06 volts, then the current Ig is 120 nanoamperes.

A pair of protective diodes 57 and 58 are connected between the output of the op amp 46 and the resistor 54. The cathode of diode 57 is connected between the op amp 46 and the resistor 54. The anode of diode 57 is connected to AV−. The anode of diode 58 is connected between the op amp 46 and the resistor 54, with the cathode of diode 58 being connected to AG. The diodes 57 and 58 are low leakage clamping diodes that conduct when the output voltage of op amp 46 is greater than 6.7 volts below virtual ground or more than 0.7 volts above virtual ground, thus protecting both the health care worker H and the device from voltage transients such as those that might be introduced should the health care worker H neglect to disconnect the monitoring device during defibrillation of the patient P.

The non-inverting input of a JFET op amp 60 is connected between the protective diodes 57 and 58 and the resistor 54. The non-inverting input of the JFET op amp 60 has an ultra high input impedance that prevents any of the current Ig from leaking. Since the inputs of op amps 46 and 60 have a high input impedance, the current Ig that flows through the gloves is the same current Ig flowing through the resistor 44. Also, since the microcontroller 20 knows the voltage output from the D/A converter 42 and the resistance of the resistor 44, the microcontroller 20 can easily determine the current Ig flowing through the gloves. If the microcontroller 20 desires to change the current Ig flowing through the gloves, then a different value is written to parallel port B 36, thus producing a different voltage output from the D/A converter 42.

The JFET op amp 60 is configured as a unity gain buffer as shown. The op amp 60 is powered by voltages AV+ and AV−. The output of the op amp 60 is connected to the inverting input of the op amp 60. A resistor 62 is connected between the output of the op amp 60 and the inverting input of an op amp 64 to establish a source impedance for op amp 64. The op amp 64 is configured as a low gain inverter and is powered by voltages AV+ and AV−. The output of the op amp 64 is connected through a feedback resistor 66 to the inverting input of the op amp 64. The non-inverting input of the op amp 64 is connected through a resistor 68 to analog ground AG, thus reducing offset bias error of op amp 64. The output of the op amp 64 produces a voltage referred to as Vg. Vg is provided to the input of one of the A/D converters in the block circuit 32 in the microcontroller 20. The microcontroller 20 periodically measures Vg to determine the resistance across the gloves being monitored, as follows. The current Ig flowing through the gloves is determined by the value written to port B 36 as was explained above. The voltage Vg is the voltage across the gloves and is directly measured, after buffering, by the A/D converter 32 inside the microcontroller 20. Therefore, the resistance across the gloves, referred to as Rn, can be calculated using Ohm's law:

$$Rn = \frac{Vg}{Ig} \text{ ohms}$$

The manner in which the microcontroller 20 periodically measures the resistance Rn across the gloves and uses the measured values to detect holes in the gloves is controlled by software stored in the ROM 26 and is explained more fully below.

Parallel port D 40 outputs three signals referred to as RED*, YEL*, and GRN*. In the discussion that follows, a signal name followed by an asterisk means that the signal is asserted when it has a logic low value. The RED* signal is provided to the cathode of a light emitting diode 70 whose anode is connected through a resistor 71 to DV+. The YEL* signal is connected to the cathode of a LED 72 whose anode is connected through a resistor 73 to DV+. The GRN* is connected to the cathode of a green LED 74 whose anode is connected through a resistor to 75 to DV+. Parallel port D also outputs a signal referred to as ALARM, which is provided through a resistor 76 to a PNP transistor 78. The collector input of the transistor 78 is connected to ground. The emitter is connected to an input of a piezo electric transducer 80. The other input to the speaker 80 is connected to +9 volts. The ALARM signal is also preferably provided to a vibrating alarm circuit 81 as shown. The vibrating alarm 81 is connected to +9 volts and ground. The BATT_LOW* signal output from the voltage converter and regulator 14 is connected to the input of port C 38. The cathode of an LED 69 is also connected to the BATT_LOW* signal. The anode of LED 69 is connected to DV+.

Software of FIGS. 2A-2D

Referring now to FIGS. 2A-D, a flowchart diagram illustrating operation of software that controls operation of the monitoring device is shown. The flowchart is shown in four portions for clarity, with interconnections between the four figures designated by reference to the circled letters A through E. The software begins operation in step 100 when the monitoring device is powered on. At power on reset, the RED*, YEL*, and GRN* signals are negated high, and thus the corresponding LEDs 70, 72, and 74 are off. Also, the ALARM signal is negated low, and thus the alarms 80 and 81 are turned off.

In step 102, the microcontroller 20 initializes various variables that are used in the software. Parallel port B 36 is initially provided with value 0, thus providing the minimum voltage output from the D/A converter 42. As previously mentioned, when port B has value 0, the actual current Ig flowing through the resistor 44 is 120 nanoamps. A value referred to as IgMAX, which represents the maximum current value of Ig, is set to $2^8-1$ or 255, which corresponds to 9.7 μA. A variable referred to as IgMIN is set to one, which corresponds to the minimum current value of 120 nanoamps. Finally, since port B is initialized to value 0, the variable Ig is initially set equal to IgMIN, which at power on reset is zero. A time variable referred to as t, which is used to keep track of the time counted by a timer in the timers block 30, is set equal to zero. Two variables referred to as Vg_LOW_THRESHOLD and Vg_HIGH_THRESHOLD are set equal to 2.5 volts and 4.375 volts, respectively. As explained below, the microcontroller 20 maintains the voltage Vg between the ranges of 2.5 volts and 4.375 volts for optimum reading of the resistance Rn across the gloves. Resistance variables referred to as Rg and RgLast are the outputs of a 2-step software filtering process that consists of a 5-point non-linear median filter, followed by a 2-stage linear averaging filter, both applied to successive values of Rn as indicated. The resistance Rg, and the first and second derivatives of Rg, are the values used by the controller 20 in determining whether a hole has formed in the gloves, as is explained below. A variable referred to as RgMIN represents the minimum observed value for the filtered resistance Rg. RgMIN is set to the highest possible value of $2^{16}-1$ at initialization. A variable referred to as dRg stores the first derivative of Rg, and a variable referred to as d²Rg stores the second derivative of Rg. A variable referred to as RgLAST, which stores the last computed value of Rg, is set equal to $2^{16}-1$, or 65,535, the highest value possible upon initialization. A variable referred to as dRgLAST stores the last value of the variable dRg that was monitored by the microcontroller 20 and is also set to $2^{16}-1$. A variable referred to as RgAVG stores the average value of Rg since the last "heartbeat" of the device, which is preferably about eight seconds. The "heartbeat" of the device refers to the fact that the green LED 74 and the transducer 80 are preferably turned on and off every eight seconds to symbolize a heartbeat for the device, i.e., to indicate that the device is operating properly. RgAVG is preferably initialized to $2^{16}-1$.

A variable referred to as ARM_PT stores a resistance value against which the resistance Rg is compared. The variable ARM_PT is preferably set to a value dependent upon perceived risk and is used to determine whether the monitoring devices should consider arming potential events. A boolean variable referred to as ARMED indicates when the device is armed, which occurs when the resistance Rg has fallen below ARM_PT and either the first or second derivatives of the resistance Rg indicate that a puncture or hole condition is likely to have occurred. During initialization, the ARMED variable is set equal to false. A variable referred to as HOLE_PT is set to a resistance indicative of a hole or puncture in the gloves, preferably set to a value dependent upon perceived risk. As explained below, when Rg drops below the HOLE_PT, and the device is armed, then the END-OF-USE ALARM is sounded. A variable referred to as HYD_PT is set to a resistance at which the glove wearer is warned that the level below which the monitoring device may not be able to reliably detect holes will be reached in the near future. This level is set depending upon perceived risk. This warning is referred to as the END-OF-USE WARNING. As explained below, when RgAVG falls below HYD_PT, and the device is unarmed, then the END-OF-USE WARNING is sounded. A variable referred to as ARMWAIT stores the length of time during which the monitoring device may be armed without detecting a hole. When the monitoring device is armed for a length of time greater than ARMWAIT, then the monitoring device becomes unarmed. The variable ARMWAIT is preferably set to 5 seconds. Variables referred to as dRg_PCT and d²Rg_PCT represent the percentage change of the value Rg_MIN that must occur in either the first or second derivatives of Rg, respectively, before the device can arm itself, as is explained below.

In step 104, the controller 20 determines the configuration values stored in the EEPROM 28 by the operator. In the preferred embodiment, two bits are used to store a possibility of four different protection configurations (0,1,2, and 3). When the two protection configuration bits have the binary value of 0, then a standard level of protection is programmed into the microcontroller 20. In this instance, the variables HOLE_PT, ARM_PT, HYD_PT, dRg_PCT, and d²Rg_PCT are set to levels appropriate to routine use. These levels may be tailored to the electrical characteristics of a particular glove, or family of gloves, or may be set at values appropriate for all gloves. The generic settings of these values at the standard level of protection are, as presently known, ARM_PT: 750 k, HYD_PT: 2.0M, HOLE_PT: 600 k, dRg_PCT: 50%, and dRg²_PCT: 50%. Accordingly, when the standard protection configuration is chosen, either the first derivative of Rg or the second derivative of Rg must be greater than 50% of Rg_MIN before the device can arm itself. If the value 1 is stored as the protection level then the settings of these values at level 1 of protection are, as presently known, ARM_PT: 1.4M, HOLE_PT: 1.2M, HYD_PT: 3.0M, dRg_PCT: 50%, and d²Rg_PCT: 50%. If the protection level is set to the value 2, then the settings of these values at level 2 of protection are, as presently known, ARM_PT: 2.6M, HOLE_PT: 2.4, HYD_PT: 4.0M, dRg_PCT: 50%, and dRg²_PCT: 50%. If the protection level is set to a value of 3, the highest protection level, then the settings of these values at level 3 of protection are, as presently known, ARM_PT: 5.0M, HOLE_PT: 4.8M, HYD_PT: 6.0M, dRg_PCT: 50% and d²Rg_PCT: 50%. The operation of the percentage values dRg_PCT and d²Rg_PCT is explained further below. It is noted that other variables such as Vg_LOW_THRESHOLD and Vg_HIGH_THRESHOLD, among others, can be modified according to the protection level configuration set out above. It is also noted that other types of risk configurations can be chosen. The following table summarizes the forgoing information regarding default settings:

|  | Level 0 | Level 1 | Level 2 | Level 3 |
| --- | --- | --- | --- | --- |
| ARM_PT | 750k | 1.4m | 2.6m | 5.0m |
| HOLE_PT | 600k | 1.2m | 2.4m | 4.8m |
| HYD_PT | 2.0m | 3.0m | 4.0m | 6.0m |
| dRg_PCT | 50% | 50% | 50% | 50% |
| d²Rg_PCT | 50% | 50% | 50% | 50% |

In step 106, the monitoring device adjusts various variables to account for various tolerances in the circuitry. Prior to operation of the device, i.e., during manufacturing and prior to step 100, each glove monitoring device is tested to account for the various tolerances in the various parts comprising the device. Preferably, a known resistance is placed across the two jacks 56 and 52 and the voltage Vg is measured. Various data are stored in the EEPROM 24 of the microcontroller 20 to indicate the amount by which the measured Vg differs from the expected value. These values are used in step 106 in order to adjust the above variables to account for the tolerances of the various components forming the device. In step 106, this data is used to alter the configuration values appropriately, and then these values are stored in the RAM 26. In step 108, a power-on indication is given by the microcontroller 20 beeping the transducer 80 and illuminating all of the LED's 70, 72 and 74. In step 110, the microcontroller 20 performs various system diagnostic checks of the various subsystems, and turns the green LED 74 and the transducer 80 on and off if the system checks OK. Preferably, the green LED 74 and the transducer 80 are turned on and off every eight seconds to symbolize a heartbeat for the device, i.e., to indicate that the device is operating properly and has passed all self-tests.

Figure 2A:
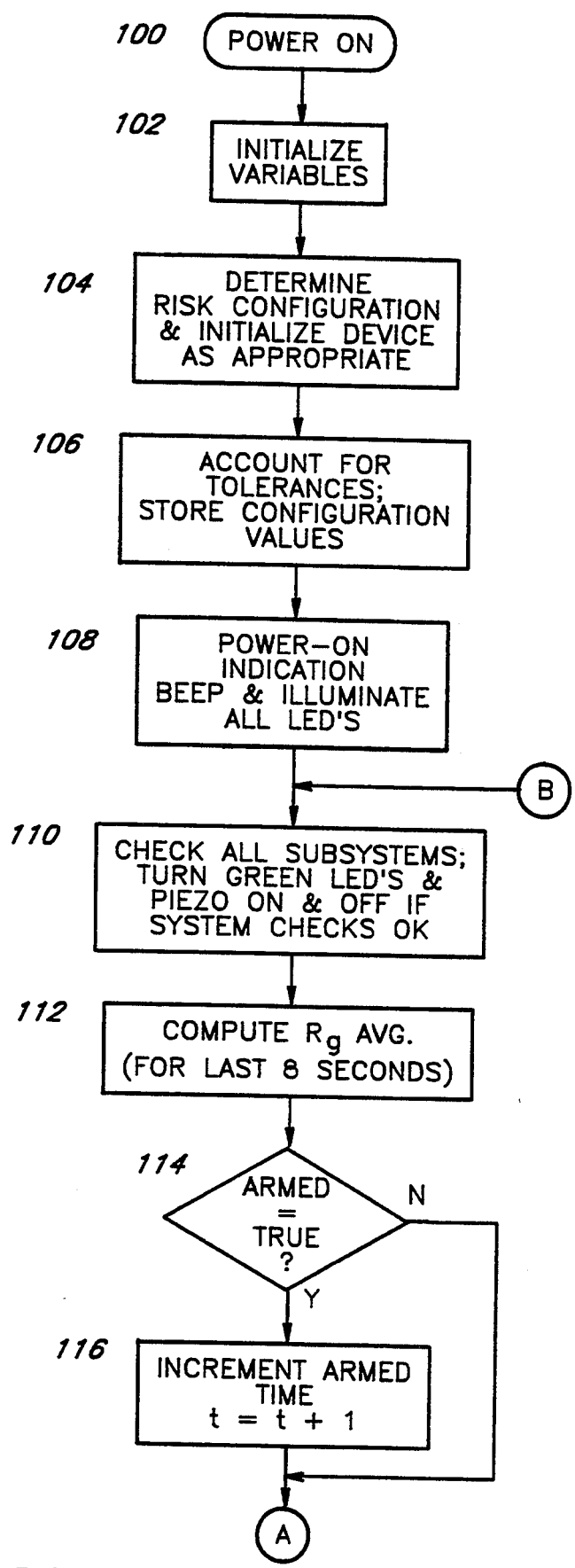
FIGS. 2A–D are flowchart diagrams illustrating operation of the monitoring device of FIG. 1.
Figure 2B:
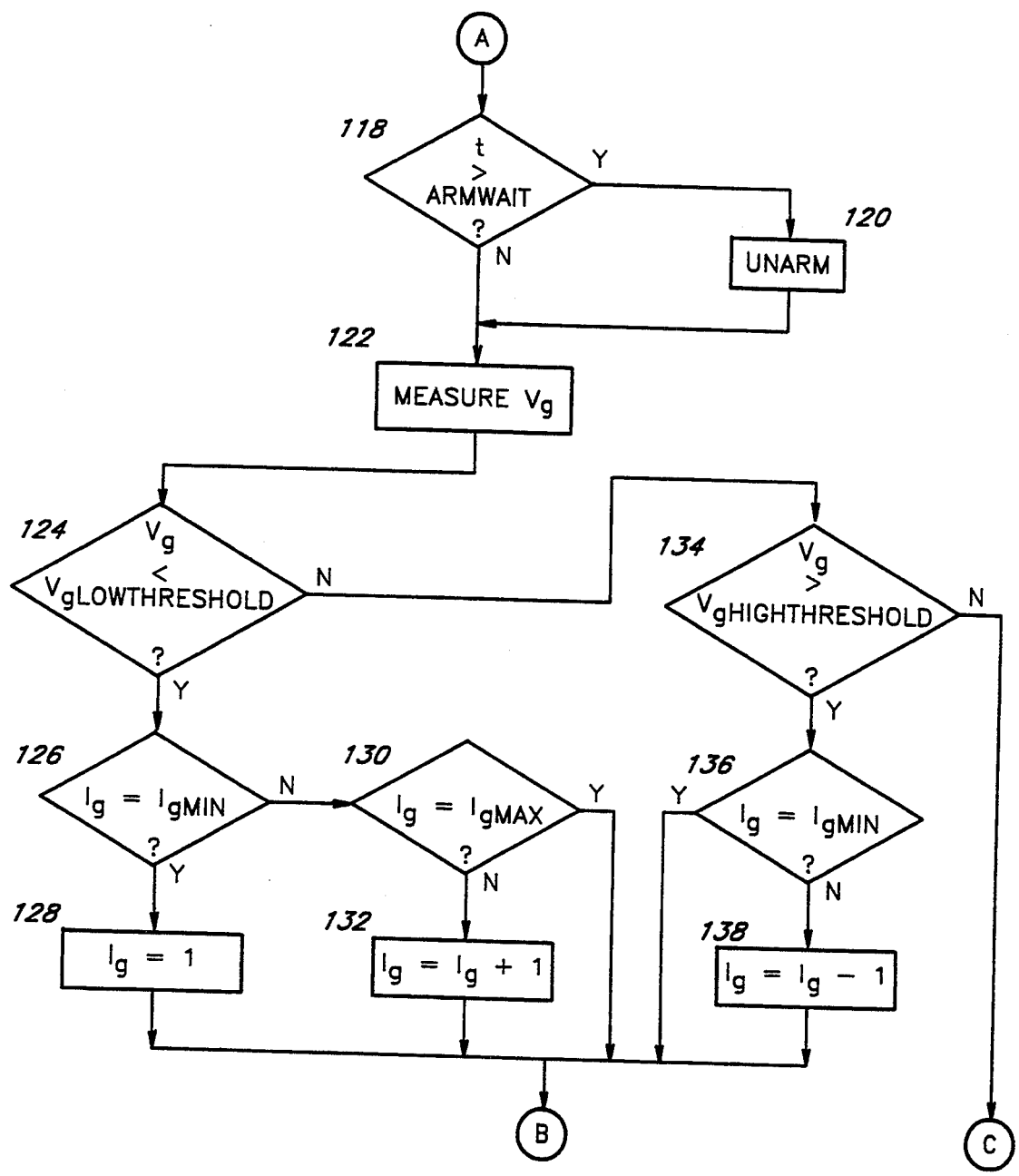

In step 112, the glove monitoring device computes RgAVG, which is the average value for Rg for the last 8 seconds. Since Rg was initialized to a certain value on power-up, and no values of Rn have yet to be taken, the initial value for RgAVG is $2^{16}-1$. In step 114, the controller 20 determines if the variable ARMED is true. If the device is ARMED in step 114, then the time variable t is incremented by 1 in step 116, and the controller 20 advances to step 118 (FIG. 2B). If the device is not ARMED in step 114, then the device advances to step 118.

In step 118, the controller 20 determines if the device has been ARMED for a period greater than ARMWAIT, which is preferably 5 seconds. If so, the device unarms itself in step 120 and then advances to step 122. If the device has not been ARMED for greater than ARMWAIT, then the device advances to step 122. In step 122, the controller 20 measures the voltage Vg received from the A/D converter in the logic block 32. In the preferred embodiment, the controller 20 takes four measurements of Vg and compares these four values. If these values differ by no more than a predetermined amount, then the four values are averaged to determine Vg for that sampling. If any pair of values of these differ by more than the preset amount, then four new values are obtained and this process is repeated. The controller 20 advances to step 124 when a new Vg value is successfully obtained.

Autorange Feature

Steps 124 through 138 comprise an autorange function wherein the controller 20, having measured the voltage Vg of the gloves, adjusts the current Ig provided to the gloves in order to retain full accuracy over the range of resistances encountered. Thus, as the resistance drops due to hydration of the gloves, the current provided to the gloves is increased to maintain the voltage Vg in the desired range. In step 124, the controller 20 determines if the voltage Vg is less than the value Vg_LOW_THRESHOLD. If the voltage Vg is determined to be less than Vg_LOW_THRESHOLD then, in step 126, the microcontroller 20 determines if the current Ig is equal to IgMIN, i.e. if value one has been written to parallel port B. As previously noted, when value one is written to port B, the current Ig is at its minimum value of 120 nanoamps. If Ig equals IgMIN in step 126, then in step 128 Ig remains at 1 and the flowchart then returns to step 110. If Ig does not equal IgMIN in step 126, then in step 128 the controller 20 determines if Ig is equal to IgMAX, which in this instance is 255, corresponding to 9.7 microamps. If Ig equals IgMAX in step 130, then the controller 120 returns to step 110. Here the current Ig cannot be increased any further to increase the voltage Vg. In practice this condition would rarely occur because in this instance the resistance Rg would be so low that an END-OF-USE WARNING would have already sounded, as is discussed below. If Ig is not equal to IgMAX in step 130, then Ig is incremented in step 132 by the controller 20 incrementing the value written to parallel port B. The controller 20 then returns to step 110. It is noted that at power-up of the system, Ig will have been set to IgMIN and thus Ig will initially be set to 1 in step 128. Thereafter the software will loop several times until Ig is incremented to such an extent that the voltage Vg is greater than Vg—LOW—THRESHOLD.

Figure 2C:
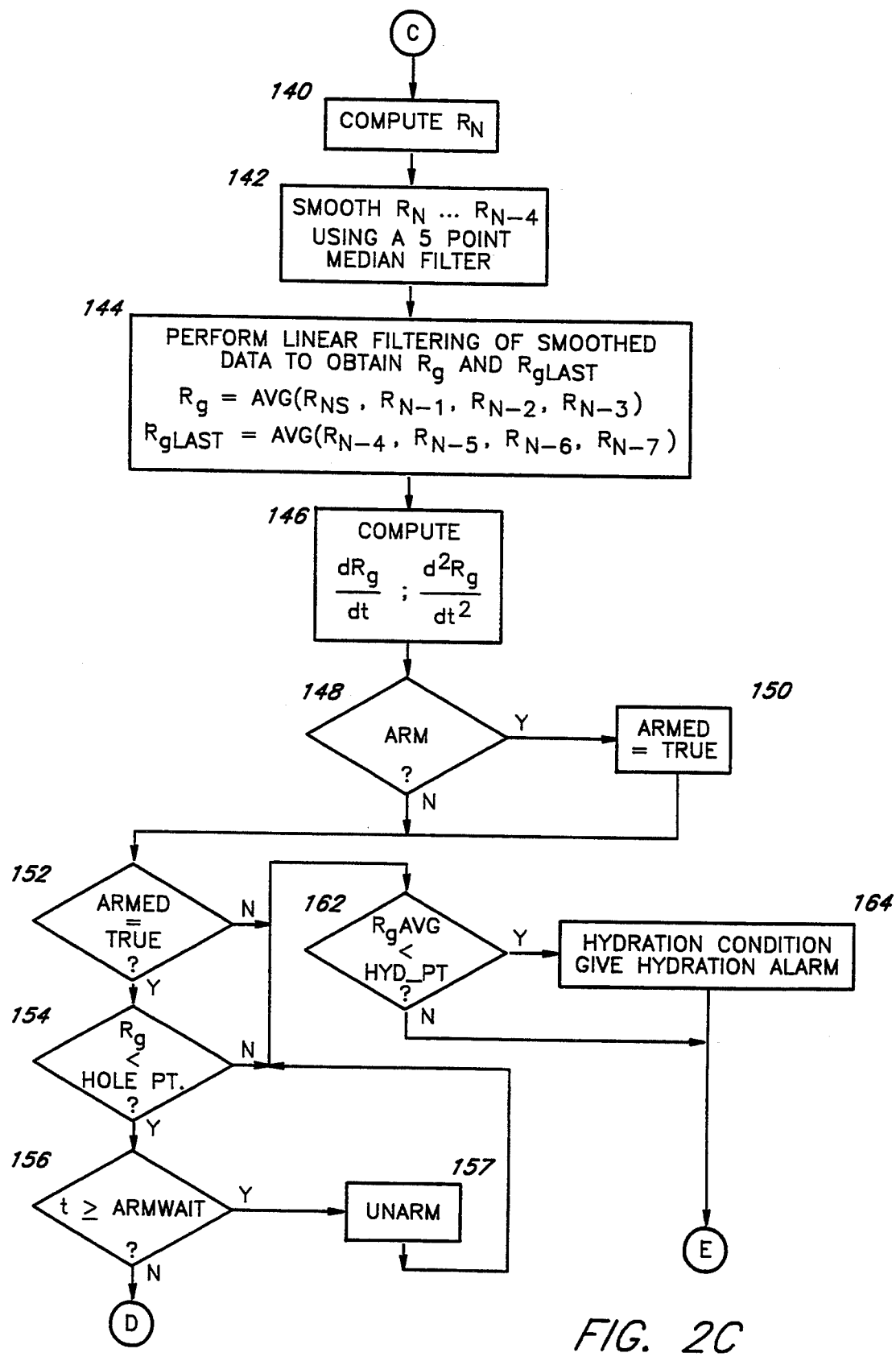

When Vg is no longer less than Vg—LOW—THRESHOLD in step 124, then in step 134, the controller 20 determines if Vg is greater than Vg—HIGH—THRESHOLD. If Vg is not greater than Vg—HIGH—THRESHOLD in step 134, then the controller advances to step 140 (FIG. 2C). If Vg is greater than Vg—HIGH—THRESHOLD in step 134, then in step 136 the controller determines if Ig is equal to IgMIN. If Ig equals IgMIN in step 136, then the resistance Rg is at a very high value. In this instance, the controller 20 returns to step 110 and repeats the process. It can be assumed that Rg will eventually decrease due to hydration of the gloves so that eventually Vg will fall below Vg—HIGH—THRESHOLD. If Ig is not equal to IgMIN in step 136, then in step 138 Ig is decremented by the controller 20 writing a value one less than the current value to port B 36.

During the remainder of the monitoring period, the autorange function in steps 124-138 maintains the voltage Vg between Vg—LOW—THRESHOLD and Vg—HIGH—THRESHOLD. Therefore, as the resistance Rg drops due to hydration, the current Ig is steadily increased to maintain Vg in the prescribed range. By maintaining Vg between this threshold, the controller 20 can read Vg more accurately, and for a longer period of time, thus increasing the length of time that the gloves can be reliably monitored. Also, the autorange function accounts for different types of gloves having varying resistances by ensuring that, regardless of the resistance of the gloves, the voltage across the gloves remains in a readable range.

As previously noted, if Vg falls between the range of Vg—LOW—THRESHOLD and Vg—HIGH—THRESHOLD in steps 124 and 134, then the controller 20 advances to step 140 in FIG. 2C. In step 140, the controller 20 computes a value for Rn, which is simply the raw resistance of the gloves. The resistance Rn is calculated according to Ohm's law:

$$Rn = Vg/Ig$$

In step 144, the controller 20 smooths the value Rn with the previous 4 values using a 5-point non-linear median filter. In other words, the values Rn, Rn-1, Rn-2, Rn-3, and Rn-4 are sorted, and the median value is selected to form a new value, this value being designated as $Rn_S$. In step 144, an averaging linear filter is used to calculate Rg and RgLast. Rg is set equal to the average of (Rns, $Rn_{S-1}$, $Rn_{S-2}$, and $Rn_{S-3}$), i.e., the average of the last four smoothed values of Rn. RgLast is set to the average of ($Rn_{S-4}$, $Rn_{S-5}$, $Rn_{S-6}$, and $Rn_{S-7}$), i.e., the average of the four smoothed values that immediately preceded the four values used to compute Rg.

In step 146, the controller 20 computes the first and second derivatives of Rg these being dRg and $d^2$Rg. These values are calculated according to the formulas:

$$dRg = max((RgLAST - Rg), 0)$$

$$d^2Rg = max((dRgLAST - dRg), 0)$$

Therefore, the first derivative of Rg, dRg, is set equal to the maximum of either the difference in Rg from the previous calculation, or zero. Likewise, the second derivative of Rg, $d^2$Rg is set equal to the maximum of either the change in the first derivative of Rg from the last calculation or zero.

In step 148, the controller 20 determines whether the monitoring device should be ARMED. This determination is based on whether the resistance Rg is less than the variable ARM—PT and either the first derivative dRg is greater than RgMIN×dRg—PCT or the second derivative $d^2$Rg is greater than the value RgMIN×$d^2$Rg—PCT. This determination can be described as follows:

$$Rg < ARM\_PT \text{ and } ((dRg) > (RgMIN \times dRg\_PCT))$$
or
$$(d^2Rg > (RgMIN \times d^2Rg\_PCT)))$$

It is noted that other criteria can be used for determining when the device should arm, such as only the change in dRg and $d^2$Rg, or just the change in $d^2$Rg alone.

Therefore, the determination of whether or not to arm is determined according to whether the resistance Rg has dropped below ARM—PT and whether the first or second derivatives have changed sufficiently with respect to the previous minimum value of RgMIN. It is noted that here the percentage factors dRg—PCT and $d^2$Rg—PCT that were chosen in step 104 and which represent the protection level configuration are utilized.

If the values for Rg, dRg, $d^2$Rg and ARM—PT are such that the monitoring device should be armed in step 148, then in step 150 the variable ARMED is set equal to TRUE, and the controller 20 advances to step 152. If the values for Rg, dRg, and $d^2$Rg are such that the device should not be ARMED in step 148, then the controller 20 advances to step 152. In step 152, the controller 20 determines if the variable ARMED is true. If the variable ARMED is true in step 152, then in step 154 the controller 20 determines if the resistance Rg is less than the value HOLE—PT. If Rg is less that HOLE—PT in step 154, then in step 156 the controller 20 determines if the device has been armed for a period of time greater than ARMWAIT. If the device has not been armed for a period greater than ARMWAIT in step 156, then in step 158 (FIG. 2D) the END-OF-USE is given. Here the transducer 80 is sounded and the red LED 70 is flashed. The controller 20 then progresses to step 160 where the value RgMIN is reset to zero, and the controller 20 then advances to step 166.

In the preferred embodiment, the END-OF-USE is sounded in step 158 when the device is armed and Rg is less than HOLE—PT. However, the END-OF-USE ALARM can be sounded based on other criteria, such as when the device is armed and either dRg or $d^2$Rg indicate that a hole has occurred. Also, the END-OF-USE ALARM can be sounded based solely on a certain amount of change in $d^2$Rg, or dRg.

Figure 2D:
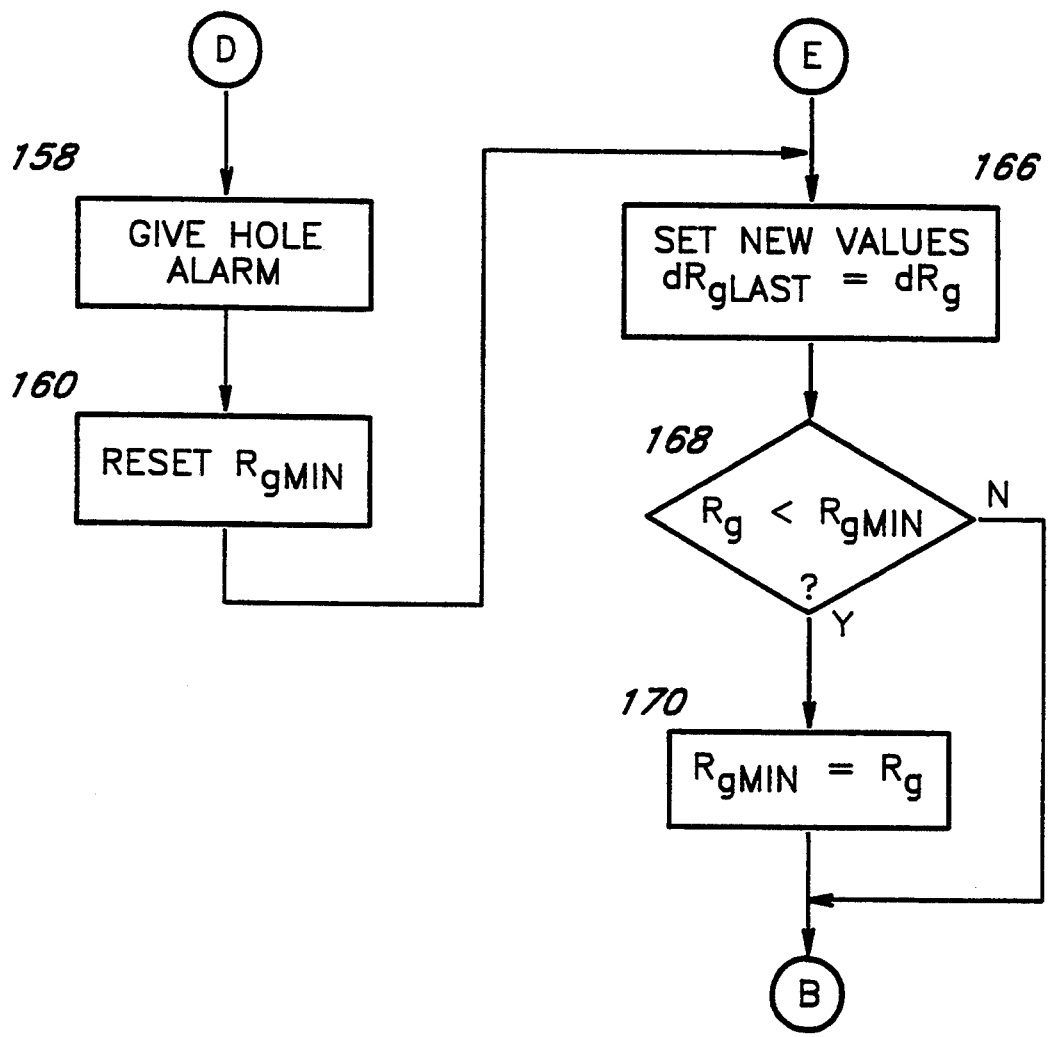
Figure 3A:
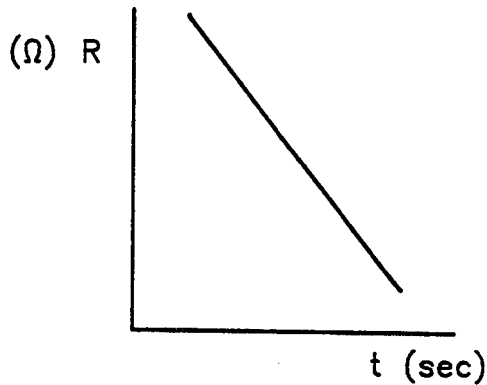
FIGS. 3A–F are various graphs illustrating resistance and the first and second derivatives of resistance across the gloves versus time during various conditions of hydration and puncture.
Figure 3B:
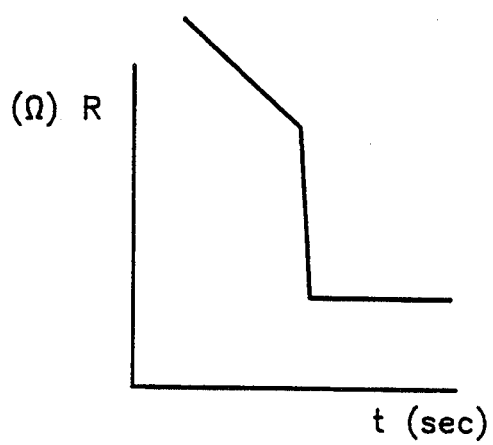
Figure 3C:
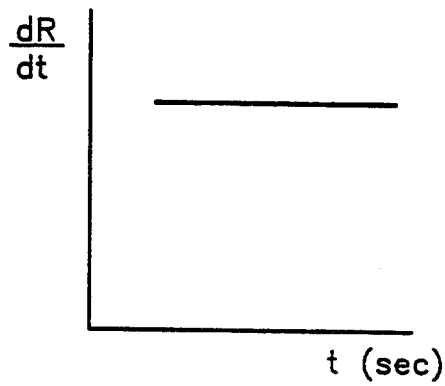
Figure 3D:
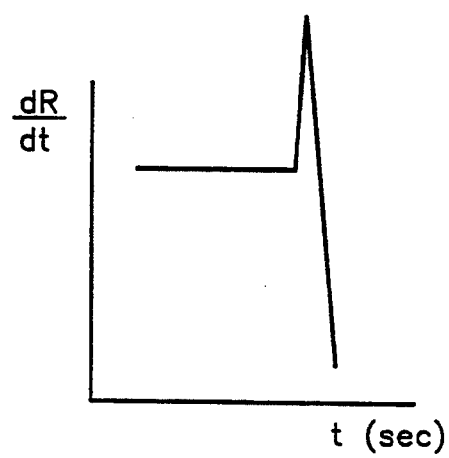
Figure 3E:
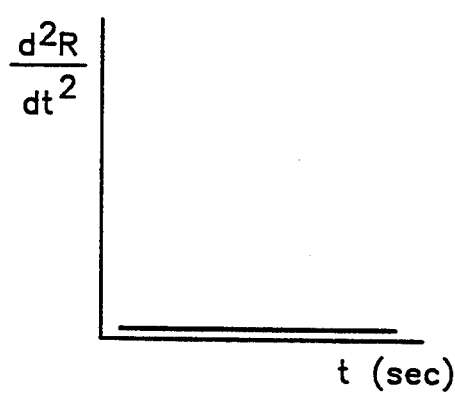
Figure 3F:
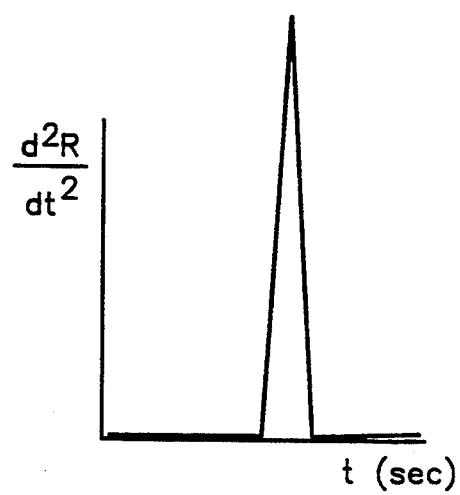
Figure 4A:
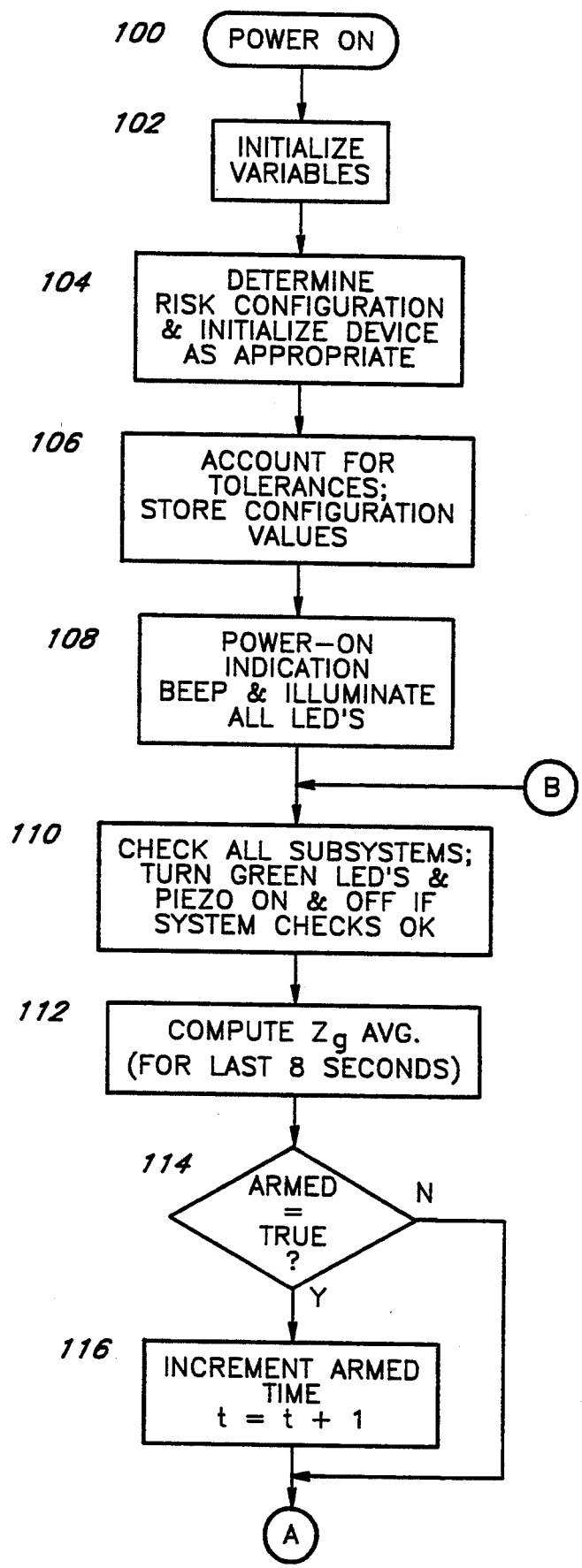
FIGS. 4A–D are flowchart diagrams illustrating operation of the monitoring device according to a second embodiment of the invention.
Figure 4B:
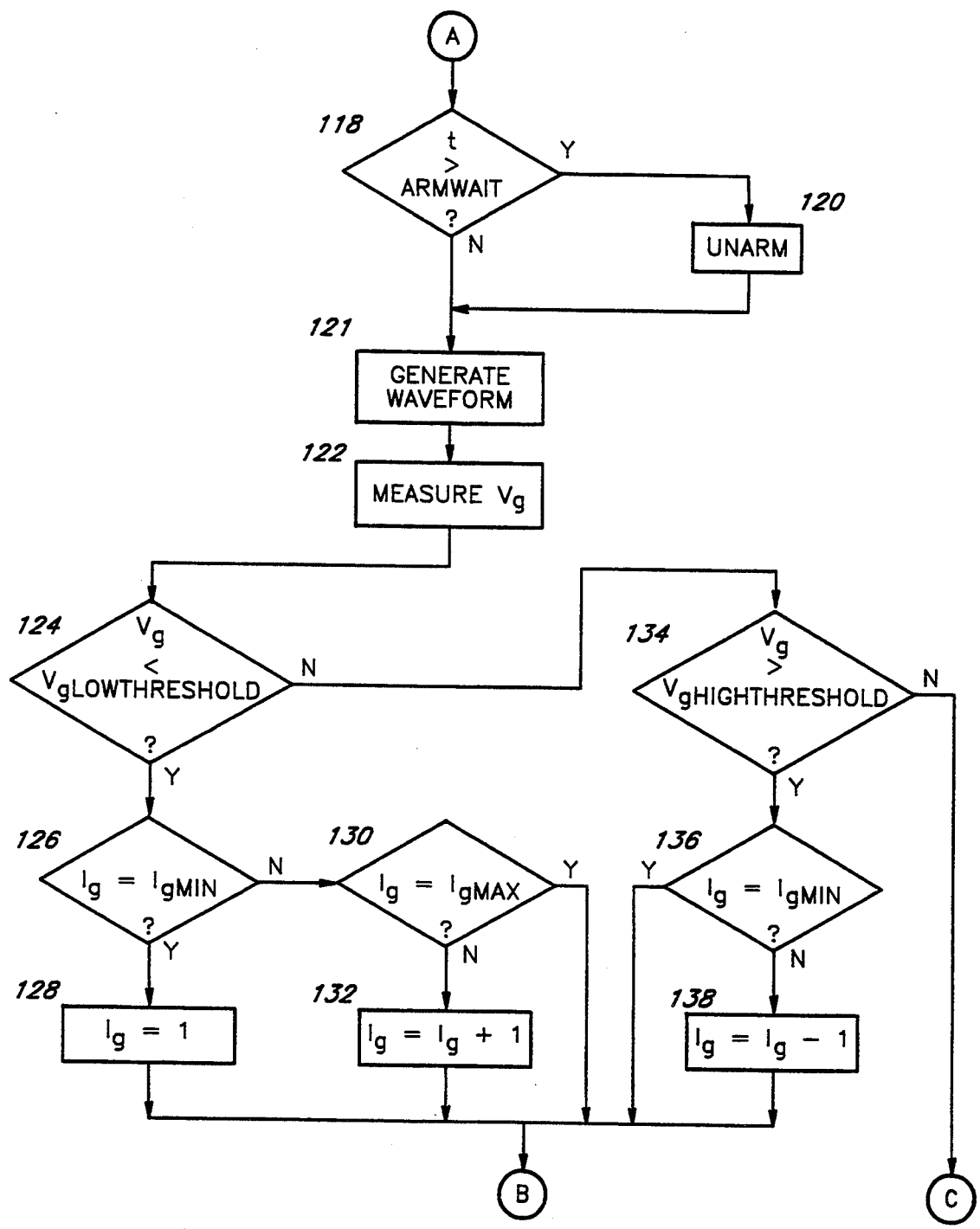
Figure 4C:
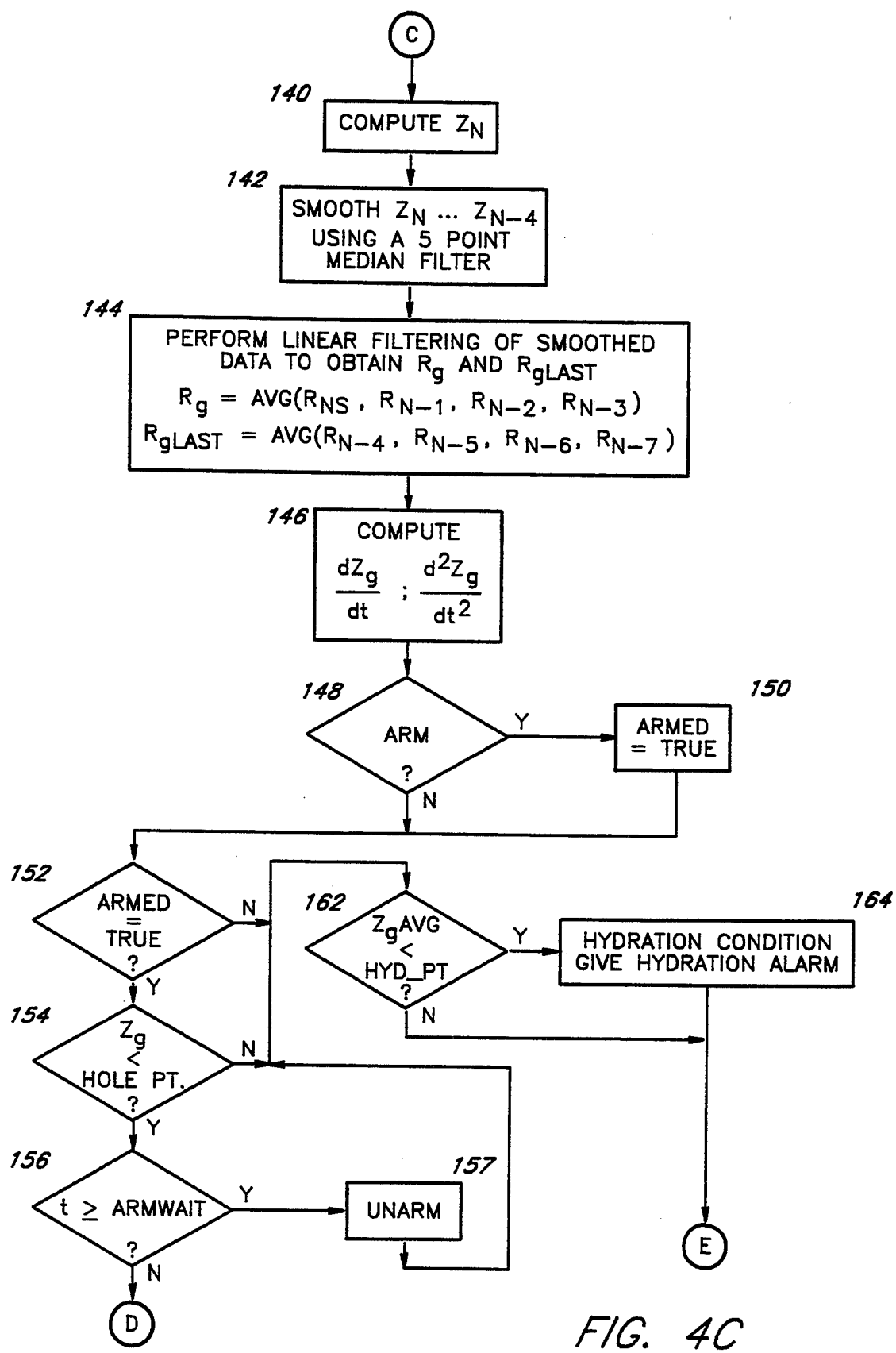
Figure 4D:
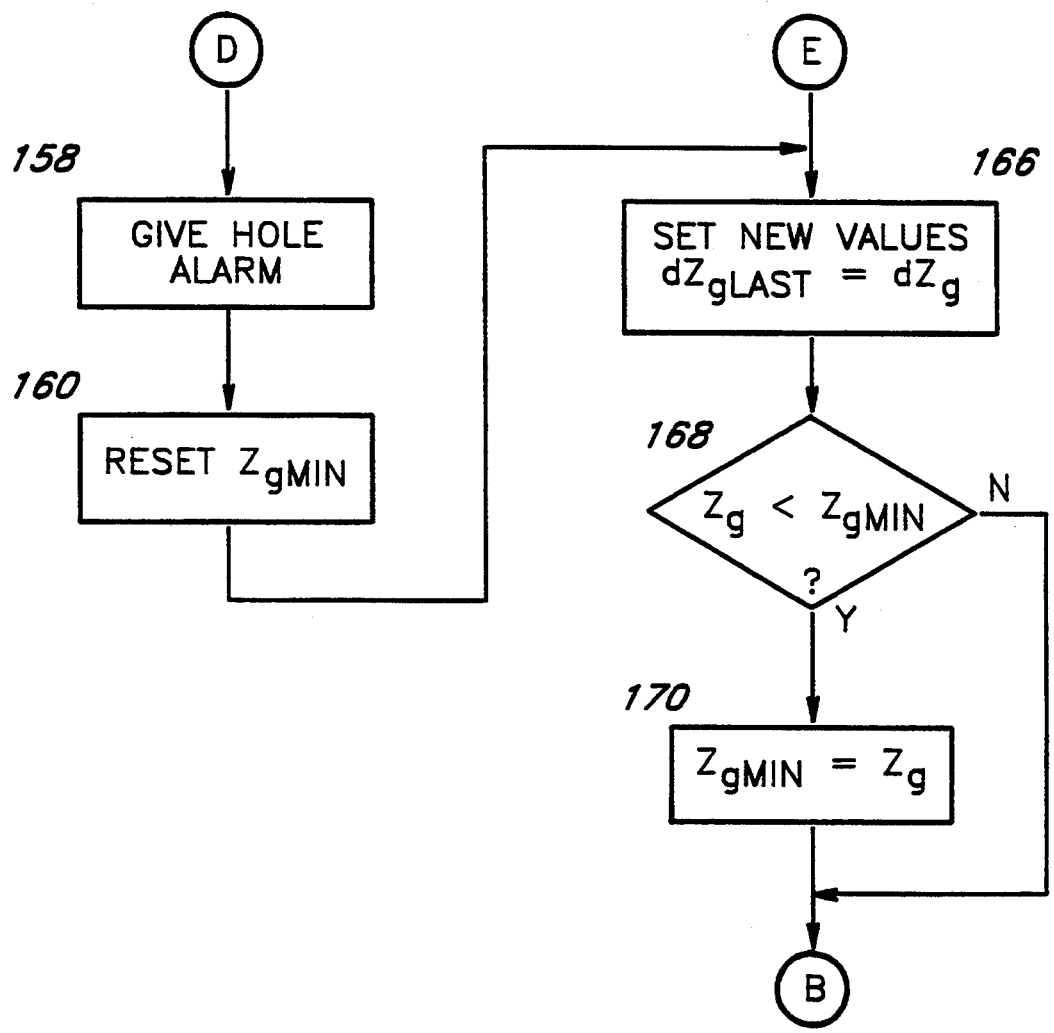

If the variable ARMED is not true in step 152 (FIG. 2C), then the controller 20 advances to step 162. Also, if the variable ARMED is true in step 152, but the resistance Rg is not less than HOLE—PT in step 154, then the controller 20 advances to step 162. If the variable t is greater than or equal to ARMWAIT in step 156, meaning that the device has been armed for greater than ARMWAIT, then in step 157 the controller 20 unarms itself and advances to step 162. In step 162, the controller 20 determines if the resistance RgAVG is less than HYD—PT. Here the controller 20 is checking to see whether the average resistance RgAVG has dropped to a point below which the glove monitoring device may no longer reasonably detect holes or punctures in the gloves. If the resistance RgAVG is less than the variable HYD_PT in step 162, then in step 164 a hydration condition has occurred, and the END-OF-USE WARNING is given. The END-OF-USE WARNING preferably includes lighting the yellow LED 72 and sounds a unique signal on the transducer 80. The controller 20 then advances to step 166 (FIG. 2D). If RgAVG is not less than HYD_PT in step 162, then the controller 20 advances to step 166.

In step 166, the controller 20 updates the variable dRgLAST to new value. The variable dRgLAST is set equal to dRg. The controller 20 then advances to step 168 where it determines if the resistance Rg is less than RgMIN. If Rg is less than RgMIN in step 168, then in step 170 RgMIN is set equal to Rg. The controller 20 then returns to step 110. If Rg is not less than RgMIN in step 168, then the controller 20 returns to step 110. Thus Rg is only altered if the new value for Rg has dropped below the previous value of RgMIN. This compensates for the problem where the surgeon withdraws his hands from the patient and thus the resistivity increases due to the surgeon's hands being away from the patient. In this instance, RgMIN will record the lowest value of Rg before the surgeon pulled his hands away from the patient. As previously noted, the variable RgMIN is used in determining whether the monitoring device should ARM in step 148 based on percentage changes in RgMIN. Therefore, the use of the variable RgMIN guarantees that when the surgeon places his hands back onto the patient, and the resistance drops dramatically because of this, the device will not ARM in step 148 because the first and second derivatives will be compared with a percentage change in the prior lowest resistance, RgMIN, not merely on the amount of change that occurred in the resistance.

The controller 20 continually progresses through steps 110 to 170, monitoring the resistance, as well as the first and second derivatives of resistance, across the gloves and using these values to determine whether a hole has occurred in the gloves. The autorange function in steps 124 to 138 maintains the measured voltage Vg in a prescribed range for a greater period of time, thus allowing the monitoring device to operate for a greater period of time. The use of the first and second derivatives allows for a more accurate determination of when adulterations or near-adulterations occur. Also, the monitoring device alerts the health care worker when the resistance across the gloves has dropped to a value at which the device can no longer reliably monitor, thus providing added safety.

Discussion of FIG. 3 Graphs

Referring now to FIG. 3, a diagram of various graphs illustrating the resistance across gloves versus time and first and second derivatives of the resistance versus time during hydration and hole conditions. As noted in FIG. 3B, it is possible to detect a hole or adulteration by examining the resistance of the gloves versus time. However, looking solely at the resistance of the gloves, a hole could be easily confused with hydration of the gloves. The first derivative of resistance versus time provides a much clearer indication of whether an adulteration has formed in a glove than does merely the resistance itself, as shown in FIG. 3D. However, it can be more easily determined as to whether an adulteration has occurred by examining the second derivative of the resistance across the gloves versus time. Here the spike in the second derivative of resistance caused by the sudden change in resistance is easily distinguished from any hydration effects of the gloves, as shown in FIGS. 3E and 3F. With respect to the "spikes" of the graphs of FIG. 3 such as FIGS. 3D and 3F, the representations illustrate the derivatives being stored as positive integers.

Regarding the embodiment of FIGS. 1 and 2A-D, it is also noted that further miniaturization of the present invention is clearly possible. Depending on business considerations, the glove monitoring device could be miniaturized down to a single integrated circuit, or to a size between the current packaging and a single circuit. If the device were to be fully miniaturized, the device and glove-wearer EKG patch could potentially be integrated, thus allowing the device to be marketed as a disposable.

The embodiments having at least certain of the features disclosed extends the functionality of the glove monitoring device to potentially allow gloves from most sources to be tested for periods of time longer than that associated with existing regloving intervals. It is further noted that the monitoring device may also be used to detect adulterations and near adulterations in other articles which act as barriers, such as condoms, surgical gowns, masks and various surgical drapes where the possibility of transmission of communicable diseases is possible.

Second Embodiment—Time-Varying Current: Measure Impedance

In an alternate embodiment of the invention, the glove monitoring device generates pulses of current, either AC or pulsating DC, in order to facilitate more accurate monitoring of the electrical properties of the gloves. This allows the glove's electrical characteristics including frequency dependent characteristics, to be fully characterized, thus providing an even greater level of testing accuracy. The operating principle of this alternate embodiment is as follows: As a glove hydrates, its DC resistance decreases, but its capacitance increases. This is due both to the increase in the dielectric constant caused by the absorbed water, and to an increase in dielectric thickness due to swelling. Since capacitive reactance (Xc) is inversely proportional to both frequency and capacitance $$Xc = \frac{1}{2\pi fC},$$

an increase in capacitance, coupled with an increase in the frequency of the applied signal, can significantly increase the "visibility" of changes in the electrical properties of the glove, particularly impedance, thus improving the detectability of a glove puncture.

The alternate embodiment preferably employs the same apparatus as that shown in FIG. 1 but uses modified controlling software. Referring now to FIGS. 4A-D, the alternate embodiment also includes a computer-controlled adaptive algorithm similar to FIGS. 2A-D of the preferred embodiment. The primary difference between this alternate embodiment as shown in FIGS. 4A-D and FIGS. 2A-D is that FIG. 4B includes an additional step, step 121, prior to step 122. In step 121, the controller 20 generates a waveform by continually changing the value written to parallel port B 36 as the software loops through the flowchart. Accordingly, the software can be designed to generate an AC signal, a pulsating DC signal, a square wave, or a variety of other waveforms. This waveform enables the second embodiment device to monitor the resistance and capacitive effects of the gloves. Thus, another difference between the embodiment shown in FIGS. 4A-D and that shown in FIGS. 2A-D is that in the embodiment of FIGS. 4A-D the device calculates the impedance Zn according to the formula:

$$Zn = \frac{Vg(t)}{Ig(t)} \text{ ohms}$$

instead of merely the resistance Rn. It is noted that since Ig is a time varying current in this alternate embodiment, both Ig and Vg are now time dependent, as shown above. Accordingly, the value Zn will include both a resistance component and a capacitive reactance component. In FIGS. 4A-D the variables Rn and Rg, as well as the other variables based on Rn and Rg, are changed to Zn and Zg, respectively.

Therefore, this alternate embodiment operates by measuring the impedance (as opposed to merely the resistance), the rate of change of that impedance, and the second derivative of impedance, across a circuit comprised of the patient, the health care worker, and the gloves worn by the health care worker. These impedance measurements take into account the resistive and capacitive reactance contributions to the glove impedance. Thus, this alternate embodiment more accurately models the glove as an electrical device in order to improve the accuracy and resolution of the measurements being made, and is designed to better distinguish between changes in the electrical properties of the glove caused by glove puncture and changes caused by glove hydration.

The operation of the second embodiment is identical to that of the first embodiment, except as has been described above.

The foregoing disclosure and description of the invention are illustrative and explanatory thereof, and various changes in the components, circuit elements, and flowcharts may be made without departing from the spirit of the invention. For example, while the technology of this invention is directed to gloves used by health care workers in the embodiments described, it is understood that the concepts and technology discussed above, such as the detection of change of electrical properties, the rate of change of electrical properties, and the second derivative of electrical properties, can be applied to other articles which serve as barriers including, but not limited to, surgical gloves, masks, drapes, condoms, clothing and other barriers. This invention as described is directed to health care where barriers such as gloves may be subjected to adulteration. Other applications include other stages in the use of such barriers including the manufacturing process.

We claim:

1. Apparatus for detecting adulteration of an article that is used as a barrier to prevent transmission of disease or other dangerous fluid between first and second persons, comprising:

an electronic circuit including a current source, first and second leads coupled to said current source for electrical attachment to the first and second persons, a detection circuit means coupled to said first and second leads, and an alarm coupled to said detection circuit means to alert either the first or second person of a condition of adulteration of the article;

said current source providing a current to said first and second leads such that a series connection is made comprising the first person, the article, and the second person such that said article has an electrical condition;

said detection circuit means monitoring the rate of the rate of change of the electrical condition of the article for detecting adulteration of the article and generating a signal indicative thereof; and said alarm receiving said adulteration indicating signal for providing an alarm when said detection circuit means detects a condition of adulteration of the article.

2. The apparatus of claim 1, wherein said detection circuit means further monitors the electrical condition and the rate of change of the electrical condition of the article in detecting adulteration and/or near-adulteration of the article.

3. The apparatus of claims 1 or 2, wherein the electrical condition monitored by said detection circuit means is resistance.

4. The apparatus of claims 1 or 2, wherein said current provided by said current source is a time-varying current; and wherein the electrical condition monitored by said detection circuit means is impedance.

5. The apparatus of claims 1 or 2, wherein said current is at a microamperage level.

6. The apparatus of claim 2, wherein said electrical condition includes voltage and current; and said detection circuit means periodically measures the voltage across the article and uses said voltage and the amount of said current to compute values representing the electrical condition of the article.

7. The apparatus of claim 6, wherein said detection circuit means periodically adjusts said current according to said measured voltage to maintain said voltage in a prescribed range.

8. The apparatus of claim 6, wherein said detection circuit means periodically calculates values for the rate of change and the rate of the rate of change of the electrical condition using said electrical condition values.

9. The apparatus of claim 8, wherein said detection circuit means stores an initial electrical condition value before a subsequent electrical condition value is computed and calculates a value for an initial rate of change of electrical condition by subtracting said subsequent electrical condition value from said initial electrical condition value.

10. The apparatus of claim 9, wherein said detection circuit means stores said initial value of the rate of change of the electrical condition before a subsequent value for the rate of change of the electrical condition is computed and calculates a value for the rate of the rate of change of the electrical condition by subtracting said subsequent value for the rate of change of the electrical condition value from said initial value for the rate of change of the electrical condition.

11. The apparatus of claim 10, wherein said detection circuit means arms if said electrical condition value is less than a first value and if either said value for the rate of change of the electrical condition is greater than a second value or said value for the rate of the rate of change of the electrical condition is greater than a third value.

12. The apparatus of claim 11, wherein means are provided for programming said second and third values to a level of protection.

13. The apparatus of claim 11, wherein said detection circuit means asserts said indicating signal if said detection circuit means is armed and a subsequent electrical condition value drops below a fourth value during a preset period of time.

14. The apparatus of claim 11, wherein said detection circuit means unarms after a period of time if during said period of time no electrical condition values have dropped below a fourth value.

15. The apparatus of claim 11, wherein said detection circuit means executes smoothing and/or filtering function or functions on a plurality of said computed electrical condition values, and wherein said detection circuit means uses said filtered electrical condition values in detecting a condition of adulteration or near adulteration of the article.

16. A method for detecting adulteration of an article which is used as a barrier to prevent transmission of disease between first and second persons, comprising the steps of:
providing current through a circuit comprised of the first person, the article, and the second person;
detecting an electrical condition, the rate of change of electrical condition, and the rate of the rate of change of electrical condition of the article; and
providing an alarm in response to a predesignated change in one or more of the electrical condition, the rate of change of electrical condition, or the rate of the rate of change of electrical condition of the article such that a condition of adulteration of the article is detected.

17. The method of claim 16, wherein the electrical condition monitored in said step of detecting is resistance.

18. The apparatus of claim 16, wherein said provided current is a time-varying current; and
wherein the electrical condition monitored in said step of detecting is impedance.

19. The method of claim 16, wherein:
said electrical condition includes voltage and current; and
said step of detecting includes periodically measuring the voltage across the article and using said voltage and the amount of said provided current to compute values representing the electrical condition of the article.

20. The method of claim 19, wherein said step of detecting further includes periodically adjusting said provided current according to said measured voltage to maintain said voltage in a prescribed range in spite of deterioration of the electrical condition of said article with time.

21. The method of claim 19, wherein said step of detecting includes periodically calculating values for the rate of change and the rate of the rate of change of the electrical condition using said electrical condition values.

22. The method of claim 21, wherein said step of detecting includes arming of said alarm if said electrical condition value is less than a first value and if either said value for the rate of change of the electrical condition is greater than a second value or said value for the rate of the rate of change of the electrical condition is greater than a third value.

23. The method of claim 22, wherein:
said second and third values are programmed based on desired level of protection.

24. The method of claim 22, wherein said step of alarm providing is performed if said step of detecting has armed said alarm and a subsequent electrical condition value drops below a fourth value during a preset period of time.

25. The method of claim 22, wherein said step of detecting includes unarming after a preset period of time if during a preset period of time no electrical condition values have dropped below a fourth value.

26. The method of claim 22, said step of detecting includes further executing smoothing and/or filtering function or functions on a plurality of said computed electrical condition values to produce filtered electrical condition values;
wherein said filtered electrical condition values are used to detect a condition of adulteration of the article.

27. A method for detecting adulteration of an article that is used as a barrier to prevent transmission of disease between persons, comprising the steps of:
providing current through a circuit comprised of a first lead, the article, and a second lead to produce an electrical condition across said article;
detecting the electrical condition, the rate of change of electrical condition, and the rate of the rate of change of electrical condition of the article; and
providing an alarm in response to a predesignated change in one or more of the electrical condition, the rate of change of electrical condition, or the rate of the rate of change of electrical condition of the article such that a condition of adulteration of the article is detected.

28. Apparatus for detecting adulteration of a glove used in critical use applications where gloves are worn by a health care worker who is exposed to the body fluids of a patient, comprising:
an electronic circuit including a current source, first and second leads coupled to the current source for electrical attachment to the health care worker and to the patient, detection circuit means coupled to said first and second leads, and an alarm coupled to said detection circuit means to alert the health care worker of a condition of adulteration of a glove;
said current source providing a current to said first and second leads such that a series connection is made comprising said first lead, the health care worker, said gloves, and the patient to create an electrical condition across said gloves;
said detection circuit means monitoring the electrical condition, the rate of change of the electrical condition, and the rate of the rate of change of the electrical condition of a glove for detecting adulteration and/or near-adulteration of a glove and generating a signal indicative thereof; and
said alarm receiving said adulteration signal for providing an alarm when said detection circuit means detects a condition of adulteration of a glove.

29. Apparatus for detecting adulteration of a glove used in critical use applications where gloves are worn by a health care worker who may be exposed to the body fluids of a patient, comprising:
an electronic circuit including a current source, first and second leads coupled to said current source for electrical attachment to the health care worker and to the patient, detection circuit means coupled to said first and second leads, and an alarm coupled to said detection circuit means to alert the health care worker of a condition of adulteration of a glove;

said current source providing a current to said first and second leads such that a series connection is made comprising said first lead, the health care worker, said gloves, and the patient;

said detection circuit means monitoring the rate of the rate of change of the electrical condition of the gloves for detecting adulteration of a glove and generating a signal indicative thereof; and said alarm receiving said indicating signal for providing an alarm when said detection circuit means detects a condition of adulteration of a glove.

30. The apparatus of claim 29, wherein said detection circuit means further monitors the electrical condition and the rate of change of the electrical condition of the gloves in detecting adulteration of a glove.

31. The structure set forth in claim 29, wherein:
a signal is provided at regular intervals to provide a periodic sign of proper operation.

32. Apparatus for detecting adulteration of an article which is used as a barrier to prevent transmission of disease between first and second persons, comprising:

an electronic circuit including a current source, first and second leads coupled to said current source for electrical attachment to the first and second persons, a detection circuit means coupled to aid first and second leads, and an alarm coupled to said detection circuit means to alert either the first or second person of a condition of adulteration of the article;

said current source providing a voltage and current to said first and second leads such that a series connection is made comprising the first person, the article, and the second person;

said detection circuit means periodically measuring said voltage across the article and using said voltage and the amount of said current to compute values representing an electrical condition of the article;

wherein the electrical condition monitored by said detection circuit means is resistance; OR wherein said current provided by said current source is a time-varying current and the electrical condition monitored by said detection circuit means is impedance;

said detection circuit means periodically adjusting said current according to said measured voltage to maintain said voltage in a prescribed range in spite of said barrier losing electrical characteristics with time;

said detection circuit means executing a smoothing function on a plurality of said computed electrical condition values to produce smoothed electrical condition values;

said detection circuit means periodically calculating values for the rate of change and the rate of the rate of change of the electrical condition using said smoothed electrical condition values;

said detection circuit means storing an initial electrical condition value before a subsequent electrical condition value is computed and calculating a value for the initial rate of change of the electrical condition by subtracting said subsequent electrical condition value from said initial electrical condition value;

said detection circuit means storing the initial value of the rate of change of the electrical condition when a subsequent value for the rate of change of the electrical condition is computed and calculating a value for the rate of the rate of change of the electrical condition by subtracting said subsequent value for the rate of change of the electrical condition value from said initial value for the rate of change of the electrical condition;

said detection circuit means arming if said electrical condition value is less than a first value and if either said value for the initial rate of change of the electrical condition is greater than a second value or said value for the rate of the rate of change of the electrical condition is greater than a third value;

wherein said second and third values are programmable based on perceived risk;

said detection circuit means unarming after a preset period of time if during said preset period of time no electrical condition values have dropped below a fourth value;

said detection circuit means asserting said indicating signal if said detection circuit means is armed and a subsequent electrical condition value drops below said fourth value during a preset period of time;

said alarm receiving said indicating signal for providing an alarm when said detection circuit means detects a condition of adulteration of the article.

* * * * *